United States Patent [19]

Takada et al.

[11] Patent Number: 5,534,430
[45] Date of Patent: Jul. 9, 1996

[54] CELL STRAIN CAPABLE OF MULTIPLYING AN EPSTEIN-BARR VIRUS

[75] Inventors: Kenzo Takada, Ube; Akiko Tochikura, Nagaokakyo; Mitsuo Yamaki, Mito, all of Japan

[73] Assignee: Hitachi Chemical Company Limited, Tokyo, Japan

[21] Appl. No.: 294,996

[22] Filed: Aug. 24, 1994

[30] Foreign Application Priority Data

Aug. 31, 1993 [JP] Japan .................................. 5-214641

[51] Int. Cl.$^6$ .............................. C12N 5/00; C12N 7/01; C12N 7/02
[52] U.S. Cl. .................... 435/240.2; 435/235.1; 435/239
[58] Field of Search ................. 435/235.1, 239, 435/240.2

[56] References Cited

U.S. PATENT DOCUMENTS

| 4,692,405 | 9/1987 | Freedman et al. | 435/7 |
| 4,916,072 | 4/1990 | Tsyi et al. | 435/240.2 |
| 5,316,920 | 5/1994 | Tedder et al. | 435/240.2 |

OTHER PUBLICATIONS

"Epstein–Barr Virus (EBV)–Negative B–Lymphoma Cell Lines for Clonal Isolation and Replication of EBV Recombinants".

Marchini, Andrew; Longnecker, Richard; Kieff, Elliott. *Journal of Virology*, Aug. 1992, p. 4972–4981.

Takada et al., Virus Genes 5:2, 147–156 (1991).

Daibata et al., Virology 196, 900–904 (1993).

Daibata et al., FASEB Journal 4:7, p. A1721, Abstract 154 (1990).

*Primary Examiner*—Michael G. Wityshyn
*Assistant Examiner*—L. Blaine Lankford
*Attorney, Agent, or Firm*—Birch, Stewart, Kolasch and Birch

[57] ABSTRACT

The present invention relates to a cell strain capable of separating and multiplying an EB virus and derived from human lymphocyte cancer cells and a method of separating and multiplying the EB virus by means of said cell strain. The present cell strain can be applied to the separation and multiplication of the wild type virus present in various places, as well as to the separation and multiplication of the virus produced by homologous recombination etc. The virus newly separated and multiplied can be applied to vaccine etc. For the more efficient separation and multiplication of the virus, several markers can be inserted into the present cell strain.

2 Claims, No Drawings

CELL STRAIN CAPABLE OF MULTIPLYING AN EPSTEIN-BARR VIRUS

FIELD OF THE INVENTION

The present invention relates to a cell strain applicable to viral diagnosis etc. of an Epstein-Barr virus (hereinafter referred to as "EB virus") and capable of effectively separating and multiplying the EB virus conventionally difficult to separate and multiply and a method of separating and multiplying the EB virus by means of said cell strain.

BACKGROUND OF THE INVENTION

The EB virus infects umbilical cord blood lymphocyte or peripheral blood lymphocyte to transform the cells. However, the EB virus generally infects cells to remain merely latent, so the infected cells hardly produce mature viruses. Although B lymphocyte cell strains (BJAR, Ramos, etc.) uninfected with the EB virus can be infected with the EB virus to continuously carry it, such strains cannot produce a large amount of EB virus (Fields, B. N. and D. M. Knipe (ed.), 1990, Virology, 2nd ed. Raven press, New York: Chapter 68, Epstein-Barr Virus, Biology, pathogenesis, and medical aspects, G. Miller, pp. 1921–1957).

Cells such as Akata, B95-8, P3HR1, etc., are known as EB virus-producing cells. In particular, Akata cells treated with anti-human immunoglobulin antibodies produce a large amount of EB virus (Takada K, Int. J. Cancer, 33, 27–32 (1984) and Takada, K. and Ono Y, J. Virol. 63, 445–449 (1989)). However, these cells are those already infected with the EB virus, and merely produce the EB virus that has already infected, and there is no report on the use of these cells to effectively separate and multiply extracellular EB viruses.

In addition, there are reports on investigations into the separation and multiplication of EB virus by means of BJAB, BL30, BL41 and Loukes, i.e. EB virus-negative B-lymphocyte cancer cells (A. Marchini, R. Longnecker and E. Kieff, J. Virol. 66, 4972–4981 (Aug. 1992)). For production of EB virus, however, these cells should be induced with a chemical substance such as 5-AZACYTIDINE, 12-O-tetradecanoylphorbol-13-acetate (TPA) etc. or with a special plasmid (pSVNaeZ), so that there are problems such as the harmful influence (safety) of the chemical substance on the human body, the poor efficiency of plasmid induction, etc., and such a cell strain for separation and multiplication of EB virus is not satisfactory in respect of the separated and multiplied viral amount.

SUMMARY OF THE INVENTION

The present invention relates to a cell strain having the ability multiply an EB virus and having the following properties (1) being derived from human lymphocyte cancer cells (AKATA cells) and (2) being uninfected with an EB virus, as well as to a method of separating and multiplying an EB virus by infecting the cell strain with an EB virus and then stimulating said infected cells with anti-human immunoglobulin to multiply the EB virus.

DETAILED DESCRIPTION OF THE INVENTION

The inventors extensively researched the means of effectively and safely separating and multiplying a large amount of EB viruses in a wide variety of samples. As a result, the inventors successfully separated an EB virus-uninfected cell strain from which the EB virus had been lost through long-term subculture in vitro of Akata cells infected with the EB virus and producing a large amount of EB virus by treatment with anti-human immunoglobulin antibodies, and they found that the cell strain thus obtained possesses the ability to effectively separate and multiply a large amount of EB virus from pharyngeal liquid.

As a parent cell for the cell strain of the invention, use is made of Akata cells i.e. known human lymphocyte cancer cells. For preparation of Akata cells from which the EB virus has been lost, a means such as long-term subculture, chemical mutagen (MNNG etc.), temperature change, UV irradiation, radiant ray irradiation, cycloheximide treatment, BZLF1 gene introduction etc. can be used singly or in combination, among which long-term subculture is used in the Examples described below.

Akata cells may be cultured in a liquid medium containing fetal bovine serum at a various concentration, preferably 10% fetal bovine serum. The cells may also be cultured in a serum-free medium or a medium containing various amino acids, sugars, etc. At intervals of 3 or 4 days the cells are dispersed in a fresh liquid medium at a cell density of $1 \times 10^4$ to $1 \times 10^6$ cells/ml, and can be cultured at a temperature of 33° C. to 40° C. Recommended culture temperature is 37° C.

As a primary screening method for the cells from which the EB virus has been lost, a means such as a technique of using, as index, reactivity in anti-human immunoglobulin treatment, fluorescent antibody technique for detection of EB virus nuclear antigens, Western blot technique, PCR (Polymerase Chain Reaction) technique, etc., may be suitably applied to the cells treated as described above, e.g. those obtained in long-term subculture mentioned above as culture type. The following examples make use of the technique of using as index the reactivity in anti-human immunoglobulin treatment.

The cell strain of the invention obtained in the above mentioned method possesses the ability multiply the EB virus.

The separation and multiplication of the EB virus by means of the cell strain of the invention may use such materials as pharyngeal liquid, blood, body fluid, tissue and cell extract, culture supernatant, etc. The following examples make use of pharyngeal liquid.

As a preferable example of the cell strain of the invention, cell strain, Clone 6, capable of multiplying the EB virus was deposited under FERM BP-4742 under the Budapest Treaty (switched from domestic deposit No. FERM P-13675) on Jun. 3, 1993 with the National Institute of Bioscience and Human-Technology, Japan.

This cell strain is a variant with diploid cells in the form of globular float, derived from human lymphocyte cancer cells (Akata cells) from which the EB virus has been lost. The cell strain may be cultured in a liquid medium containing e.g. fetal bovine serum at a various concentration, preferably a PRMI1640 medium containing 10% fetal bovine serum. For subculture, the cells are dispersed in a fresh medium at intervals of 3 or 4 days at a cell density of $1 \times 10^4$ to $1 \times 10^6$ cells/ml, and may be cultured at a temperature of 33° C. to 40° C., preferably 37° C. This cell strain can be stored in liquid nitrogen for a long period.

The separation and multiplication of the EB virus by means of the cell strain of the invention comprises infecting the cell strain of the invention with the EB virus (e.g. the EB virus-containing materials described above) and then treating it with anti-human immunoglobulin antibodies so that the EB virus can be produced in a large amount. The EB virus thus obtained can be applied to a wide variety of utilities. In addition, the cell strain can also be applied owing to its properties to viral diagnosis of EB virus.

The cell strain of the invention enables the EB virus in various samples to be separated and multiplied in a large amount. Thus, the present cell strain can be applied to the separation and multiplication of the wild type virus present in various places, as well as to the separation and multiplication of the virus produced by homologous recombination etc. The virus newly separated and multiplied can be applied to a vaccine etc. For the more efficient separation and multiplication of the virus, several markers can be inserted into the present cell strain. The resulting EB virus can be used as a vector for gene therapy.

EXAMPLES

Example 1

A cell clone from which the EB virus had been lost through the long subculture of Akata cells was separated in the following manner. Subculture was repeated in a frequency of 2 or 3 times a week for 5 years to give a cell population about 60% of which was found to be EB virus-negative by fluorescent antibody staining. Subsequently, the EB virus-negative cell population was suspended in a liquid medium composed of 50% conditioned liquid medium (supernatant of Akata cell culture) and 50% liquid medium PRMI1640 containing 20% fetal bovine serum, and was then inoculated onto a 96-well plate such that 0.5 cell (200 μl cell suspension) was put into each well, and the suspension was thus inoculated onto four 96-well plates. After inoculation, the cells were cultured in 5% carbon dioxide gas at 37° C. under saturated humidity. Half the liquid medium was replaced by fresh one at intervals of 3 or 4 days. 3 weeks thereafter, cell growth was observed in about 50% of the wells. Among them, the clones in 56 wells where cell growth was observed as single colony were evaluated for EB virus nuclear antigens (EBNA) by fluorescent antibody technique. As a result, 28 clones were found to be EB virus (EBNA)-negative, out of which 5 clones (Clone Nos. 5, 6, 9, 13, and 14) were ascertained to be EB virus antigen-negative by Western blot technique and EB virus DNA-negative by Southern blot and PCR techniques.

Example 2

The EB virus in B95-8 cell culture supernatant as a standard virus strain was inoculated onto Clone 6 separated and multiplied in Example 1, and the cells were cultured in 5% carbon dioxide gas at 37° C. under saturated humidity. After culture for 2 days, fluorescent antibody staining indicated that about 30% cells are EB virus nuclear antigens (EBNA)-positive. Then, anti-human immunoglobulin antibodies (Kappel Co., Ltd.) were added thereto and the cells were cultured for additional 2 days. Using fluorescent antibody technique, the cells were examined for VCA (virus capsid antigens) i.e. a marker of virus production. As a result, about 13% cells were VCA-positive and it was ascertained that the present cells are suitable for the separation and multiplication of EB virus.

Example 3

Pharyngeal liquid was inoculated onto Clone 6 separated in Example 1 and then cultured for about 2 months. Fluorescent antibody staining showed that about 30% cells are EB virus nuclear antigens (EBNA)-positive. Then, pharyngeal liquid-derived EB viruses were produced by treatment with anti-human immunoglobulin antibodies (Kappel Co., Ltd.). 2 days after anti-human immuno-globulin treatment, about 21% cells were VCA-positive and produced the virus. The amount of virus produced was 20 μg in terms of viral DNA contained in 1 liter of the culture liquid, and this level was about twice as much as that of B95-8cells. From this finding, it was ascertained that the EB virus in pharyngeal liquid can be separated and multiplied in a large amount by means of the EB virus-negative cell strain separated and multiplied from Akata cells.

What is claimed is:

1. A cell line which is deposited under the accession number FERM BP-4742.

2. A cell line comprising cells having all of the identifying characteristics of cells of the cell line deposited as FERM BP4742.

* * * * *